United States Patent
Sharma et al.

(10) Patent No.: US 9,439,435 B2
(45) Date of Patent: *Sep. 13, 2016

(54) METHOD FOR CONTROLLING WEEDS USING FORMULATIONS CONTAINING FLUTHIACET-METHYL AND HPPD HERBICIDES

(71) Applicant: FMC Corporation, Philadelphia, PA (US)

(72) Inventors: Shiv D. Sharma, Philadelphia, PA (US); Gail G. Stratman, Stromsburg, NE (US); Kumar Vankayala, Bangalore (IN); Sarwar Rahi, Lahore (PK)

(73) Assignee: FMC Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/797,943

(22) Filed: Jul. 13, 2015

(65) Prior Publication Data

US 2015/0313235 A1 Nov. 5, 2015

Related U.S. Application Data

(63) Continuation of application No. 14/218,283, filed on Mar. 18, 2014, now Pat. No. 9,078,443.

(30) Foreign Application Priority Data

Jan. 31, 2014 (IN) .............................. 134/KOL/2014

(51) Int. Cl.
| | | |
|---|---|---|
| *A01N 41/10* | (2006.01) | |
| *A01N 43/68* | (2006.01) | |
| *A01N 43/80* | (2006.01) | |
| *A01N 43/90* | (2006.01) | |
| *A01N 43/653* | (2006.01) | |

(52) U.S. Cl.
CPC .............. *A01N 43/90* (2013.01); *A01N 41/10* (2013.01); *A01N 43/653* (2013.01); *A01N 43/80* (2013.01)

(58) Field of Classification Search
None
See application file for complete search history.

(56) References Cited

U.S. PATENT DOCUMENTS

| | | |
|---|---|---|
| 6,413,907 B2 | 7/2002 | Ruegg |
| 6,583,087 B2 | 6/2003 | Ueda |
| 6,734,139 B1 | 5/2004 | Feucht et al. |
| 6,841,517 B1 | 1/2005 | Feucht et al. |
| 6,908,883 B2 | 6/2005 | Sievernich et al. |
| 7,632,782 B2 | 12/2009 | O'Neal et al. |
| 7,648,945 B2 | 1/2010 | Hills et al. |
| 8,003,569 B2 | 8/2011 | Witschel et al. |
| 8,283,291 B2 | 10/2012 | Yamaji et al. |
| 8,404,933 B2 | 3/2013 | Chen et al. |
| 8,466,088 B2 | 6/2013 | Shimoharada et al. |
| 8,609,935 B2 | 12/2013 | Kinney et al. |
| 9,078,443 B1* | 7/2015 | Sharma .................. A01N 43/90 |
| 2002/0004457 A1* | 1/2002 | Nevill ..................... A01N 61/00 504/138 |
| 2003/0041357 A1 | 2/2003 | Jepson et al. |
| 2004/0116294 A1 | 6/2004 | Feucht et al. |
| 2004/0259732 A1 | 12/2004 | Asrar et al. |
| 2005/0090396 A1 | 4/2005 | Feucht et al. |
| 2005/0090397 A1 | 4/2005 | Feucht et al. |
| 2005/0192182 A1 | 9/2005 | Feucht et al. |
| 2005/0239654 A1 | 10/2005 | Kibler et al. |
| 2006/0009358 A1 | 1/2006 | Kibler et al. |
| 2007/0010397 A1 | 1/2007 | Goto et al. |
| 2008/0242544 A1 | 10/2008 | Duckham et al. |
| 2008/0300139 A1 | 12/2008 | Zawierucha et al. |
| 2009/0029857 A1 | 1/2009 | Meazza et al. |
| 2010/0093715 A1 | 4/2010 | Voeste et al. |
| 2010/0113274 A1 | 5/2010 | Hemminghaus et al. |
| 2010/0113513 A1* | 5/2010 | Murphy Kessabi ... A01N 43/42 514/311 |
| 2010/0190794 A1 | 7/2010 | Hupe et al. |
| 2010/0210462 A1 | 8/2010 | Yamato |
| 2010/0248963 A1 | 9/2010 | Becher et al. |
| 2010/0248964 A1 | 9/2010 | Yamato |
| 2010/0285961 A1 | 11/2010 | Hacker et al. |
| 2010/0298142 A1 | 11/2010 | Yamato |
| 2011/0294662 A1 | 12/2011 | Seitz et al. |
| 2011/0319266 A1 | 12/2011 | Yamato et al. |
| 2012/0040830 A1 | 2/2012 | Zhu et al. |
| 2012/0110701 A1 | 5/2012 | Garizi et al. |
| 2012/0110702 A1 | 5/2012 | Yap et al. |
| 2012/0195974 A1 | 8/2012 | Yadav et al. |
| 2012/0283099 A1 | 11/2012 | Roy et al. |
| 2012/0283100 A1 | 11/2012 | Roy et al. |
| 2012/0329649 A1 | 12/2012 | Hunter et al. |
| 2013/0019348 A1 | 1/2013 | Crouse et al. |
| 2013/0023413 A1 | 1/2013 | Hacker et al. |
| 2013/0029847 A1 | 1/2013 | Findley et al. |

(Continued)

FOREIGN PATENT DOCUMENTS

| | | |
|---|---|---|
| CN | 1409965 A | 4/2003 |
| WO | 03/047340 A2 | 6/2003 |

OTHER PUBLICATIONS

International Search Report and Written Opinion issued on Mar. 4, 2015 in connnection with International Patetn Application No. PCT/US2015/013218 (14 pages).

New Synergistic and selective herbicide compositions, Research Disclosure, Mason Publications, No. 452, p. 2044, Dec. 2001, GB XP001087222.

(Continued)

*Primary Examiner* — Alton Pryor

(57) ABSTRACT

Methods for controlling weeds in a crop by applying to weeds having an average height ranging from about 4 inches to about 8 inches a herbicidally effective amount of a composition that includes (a) fluthiacet-methyl and (b) a p-hydroxyphenylpyruvate dioxygenase (HPPD) inhibitor are presented.

16 Claims, No Drawings

(56) References Cited

U.S. PATENT DOCUMENTS

| | | |
|---|---|---|
| 2013/0109566 A1 | 5/2013 | Niyaz et al. |
| 2013/0288893 A1 | 10/2013 | Buysse et al. |
| 2014/0013654 A1 | 1/2014 | Burke |
| 2014/0024527 A1 | 1/2014 | Stevenson |

OTHER PUBLICATIONS

Colby S. R. "Calculating Synergistic and Antagonistic Responses of Herbicide Combinations" WEES vol. 15, No. 1, Jan. 1967, pp. 20-22.

* cited by examiner

METHOD FOR CONTROLLING WEEDS USING FORMULATIONS CONTAINING FLUTHIACET-METHYL AND HPPD HERBICIDES

FIELD OF THE DISCLOSED SUBJECT MATTER

The presently disclosed subject matter relates to compositions containing fluthiacet-methyl and p-hydroxyphenylpyruvate di oxygenase (HPPD) inhibitors, and methods for controlling weeds using those compositions.

BACKGROUND

One of the more preferred methods of controlling weeds in crops involves the post-emergent control of weeds wherein herbicide(s) are applied after the crop in question has emerged from the soil. Post-emergent control is desirable as it requires the application of herbicide only where an infestation of weeds is present. In contrast, pre-emergent control requires the application of herbicide early in the growing season before most weeds have germinated, with the result that such chemicals must be employed throughout a field even if they would ultimately not be needed.

Fluthiacet-methyl, or methyl [[2-chloro-4-fluoro-5-[(tetrahydro-3-oxo-1H,3H-[1,3,4]thiadiazolo[3,4-a]pyridazin-1-ylidene)amino]phenyl]thio]acetate, is an effective post-emergent herbicide for a number of weeds, particularly broadleaf weeds.

p-Hydroxyphenylpyruvate dioxygenase (HPPD) is an enzyme found in both plants and animals, which catalyzes the catabolism of the amino acids phenylalanine and tyrosine. Inhibition of this enzyme has profound effects on plants, affecting the formation of homogentisic acid which is a key precursor for the biosynthesis of both tocopherols (vitamin E) and plastoquinone, a critical co-factor in the formation of carotenoids, which protect chlorophyll in plants from being destroyed by sunlight.

SUMMARY OF THE DISCLOSED SUBJECT MATTER

It has now been discovered that fluthiacet-methyl, when used in combination with a para-hydroxyphenylpyruvate dioxygenase (HPPD) inhibitor, is surprisingly effective at controlling broadleaf weeds having an average height ranging from about 4 inches to about 8 inches.

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof.

In one embodiment, the present disclosure describes an agricultural formulation or tank mix containing at least two agriculturally active ingredients: fluthiacet-methyl and an HPPD inhibitor. In an embodiment, the HPPD inhibitor is selected from mesotrione, sulcotrione, nitisinine, tembotrione, topramezone, fenquinotrione, ketospiradox, and tefuryltrione. In another embodiment, the HPPD inhibitor is preferably mesotrione. According to one aspect of this embodiment, the fluthiacet-methyl and the HPPD inhibitor are present in a ratio between about 1:2 and about 1:60 by weight. In a preferred aspect, the fluthiacet-methyl and the HPPD inhibitor are present in a ratio between about 1:10 and about 1:40. In a more preferred aspect, the fluthiacet-methyl and the HPPD inhibitor are present in a ratio between about 1:15 and about 1:35. These can be commercial formulations that are tank mixed at the time of application or more preferably a suspension concentrate premix formulation. In a further aspect, the agricultural formulation or tank mix contains an additional crop protection agent. The additional crop protection agent can be selected from the group consisting of atrazine, glyphosate, glufosinate, pyroxasulfone, dicamba, diflufenzopyr, nicosulfuron, salts thereof, and mixtures of two or more thereof. In one aspect the additional crop protection agent is atrazine.

In another embodiment, the present disclosure presents a method for controlling weeds having an average height ranging from about 4 inches to about 8 inches in a crop, wherein the method includes the step of applying to weeds having an average height ranging from about 4 inches to about 8 inches a herbicidally effective amount of a composition or tank mix comprising fluthiacet-methyl and an HPPD inhibitor. The HPPD inhibitor can be mesotrione, sulcotrione, nitisinine, tembotrione, topramezone, fenquinotrione, ketospiradox or tefuryltrione, and is preferably mesotrione. According to one aspect of this embodiment, the fluthiacet-methyl and the HPPD inhibitor are present in a ratio between about 1:2 and about 1:60 by weight. In a preferred aspect, the fluthiacet-methyl and the HPPD inhibitor are present in a ratio between about 1:10 and about 1:40. In a more preferred aspect, the fluthiacet-methyl and the HPPD inhibitor are present in a ratio between about 1:15 and about 1:35. In another embodiment, the disclosure provides for methods for making formulations comprising fluthiacet-methyl and an HPPD inhibitor. These can be commercial formulations that are tank mixed at the time of application or more preferably a suspension concentrate premix formulation. In a further aspect, the composition can contain an additional crop protection agent. In another embodiment, the additional crop protection agent is selected from atrazine, glyphosate, glufosinate, pyroxasulfone, dicamba, diflufenzopyr, nicosulfuron, salts thereof, and mixtures of two or more thereof. In a preferred aspect, the additional crop protection agent is atrazine.

DETAILED DESCRIPTION

The compositions of this disclosure include mixtures of fluthiacet-methyl and a HPPD (p-hydroxyphenylpyruvate dioxygenase) inhibitor herbicide. In one embodiment, the ratio of fluthiacet-methyl to HPPD inhibitor is about 1:2 to about 1:60 by weight, preferably about 1:10 to about 1:40 and most preferred about 1:15 to about 1:35 by weight. In another embodiment the ratio of fluthiacet-methyl to HPPD inhibitor is about 1:17.5 by weight. In another embodiment the ratio of fluthiacet-methyl to HPPD inhibitor is about 1:32.5 by weight. These can be commercial formulations that are tank mixed at the time of application, or more preferably, a suspension concentrate premix formulation. HPPD herbicides include mesotrione, sulcotrione, nitisinine, tembotrione, topramezone, fenquinotrione, ketospiradox and tefuryltrione. Preferably, the HPPD herbicide is mesotrione.

The compositions of the present disclosure can be in any conventional agriculturally useful form, for example, in the form of a twin pack, or in a ready-to-use formulation, or in the form of a tank mix. Additionally, the active compounds can be supplied (either separately or pre-mixed) in any appropriate formulation type, for example an emulsion concentrate (EC), a suspension concentrate (SC), a suspoemulsion (SE), a capsule suspension (CS), a water dispersible granule (WG), an emulsifiable granule (EG), a water in oil emulsion (EO), an oil in water emulsion (EW), a microemulsion (ME), an oil dispersion (OD), an oil miscible flowable (OF), an oil miscible liquid (OL), a soluble concentrate (SL), an ultra-low volume suspension (SU), an ultra-low volume liquid (UL), a dispersible concentrate (DC), a wettable powder (WP) or any other technically feasible formulation in combination with agriculturally acceptable adjuvants. For tank mixing, commercial formulations of fluthiacet-methyl (CADET®) and the HPPD herbicide (for example, mesotrione, commercial formulation CALLISTO®) are combined in a tank prior to application, in the appropriate ratio to provide the targeted weight ratio of the active ingredients. In one preferred embodiment, the compositions of the present disclosure are supplied as pre-mix suspension concentrates.

The compositions and tank mixes of the present disclosure are useful for the control of susceptible weed species in crops such as corn and sugar cane. Susceptible weeds include waterhemp, lambsquarters, velvetleaf, palmer amaranth, pigweed, morning glory, cocklebur, ragweed, broadleaf signalgrass, foxtail, crabgrass, volunteer soybean, nutsedge, Egyptian crowfoot grass, fumitory, denticulate medick, lesser swine cress, brown beetle grass, jungle grass, tendla, false amaranth, common purslane and field bindweed, having an average weed height of about 4 inches to about 8 inches. In one embodiment, the average weed height is about 4 inches to about 6 inches; in a preferred embodiment the average weed height is about 4 to about 5 inches. In another embodiment, the average weed height is selected from about 4 to about 7 inches, or about 5 to about 6 inches, or about 5 to about 7 inches, or about 5 to about 8 inches, or about 6 to about 7 inches, or about 6 to about 8 inches, or about 7 to about 8 inches.

Rates of application of the composition, or tank-mixed separately formulated active ingredients, will vary according to prevailing conditions such as targeted weeds, degree of infestation, weather conditions, soil conditions, crop species, mode of application, and application time. Compositions containing fluthiacet-methyl and an HPPD inhibitor can be applied as sprays, such as water-dispersible concentrates, wettable powders, or water-dispersible granules. In one embodiment, the rate of application for active ingredient ("ai") (e.g. fluthiacet-methyl and an HPPD inhibitor) is from about 10 g ai/acre to about 500 g ai/acre, preferably about 50 g ai/acre to about 120 g ai/acre.

The compositions and tank mixes of the present disclosure can additionally comprise further crop protection agents. Suitable crop protection active ingredients for the formulations of the present disclosure include the following:

Insecticides: A1) the class of carbamates consisting of aldicarb, alanycarb, benfuracarb, carbaryl, carbofuran, carbosulfan, methiocarb, methomyl, oxamyl, pirimicarb, propoxur and thiodicarb; A2) the class of organophosphates consisting of acephate, azinphos-ethyl, azinphos-methyl, chlorfenvinphos, chlorpyrifos, chlorpyrifos-methyl, demeton-S-methyl, diazinon, dichlorvos/DDVP, dicrotophos, dimethoate, disulfoton, ethion, fenitrothion, fenthion, isoxathion, malathion, methamidaphos, methidathion, mevinphos, monocrotophos, oxymethoate, oxydemetonmethyl, parathion, parathion-methyl, phenthoate, phorate, phosalone, phosmet, phosphamidon, pirimiphos-methyl, quinalphos, terbufos, tetrachlorvinphos, triazophos and trichlorfon; A3) the class of cyclodiene organochlorine compounds such as endosulfan; A4) the class of fiproles consisting of ethiprole, fipronil, pyrafluprole and pyriprole; A5) the class of neonicotinoids consisting of acetamiprid, chlothianidin, dinotefuran, imidacloprid, nitenpyram, thiacloprid and thiamethoxam; A6) the class of spinosyns such as spinosad and spinetoram; A7) chloride channel activators from the class of mectins consisting of abamectin, emamectin benzoate, ivermectin, lepimectin and milbemectin; A8) juvenile hormone mimics such as hydroprene, kinoprene, methoprene, fenoxycarb and pyriproxyfen; A9) selective homopteran feeding blockers such as pymetrozine, flonicamid and pyrifluquinazon; A10) mite growth inhibitors such as clofentezine, hexythiazox and etoxazole; A11) inhibitors of mitochondrial ATP synthase such as diafenthiuron, fenbutatin oxide and propargite; uncouplers of oxidative phosphorylation such as chlorfenapyr; A12) nicotinic acetylcholine receptor channel blockers such as bensultap, cartap hydrochloride, thiocyclam and thiosultap sodium; A13) inhibitors of the chitin biosynthesis type 0 from the benzoylurea class consisting of bistrifluron, diflubenzuron, flufenoxuron, hexaflumuron, lufenuron, novaluron and teflubenzuron; A14) inhibitors of the chitin biosynthesis type 1 such as buprofezin; A15) moulting disruptors such as cyromazine; A16) ecdyson receptor agonists such as methoxyfenozide, tebufenozide, halofenozide and chromafenozide; A17) octopamin receptor agonists such as amitraz; A18) mitochondrial complex electron transport inhibitors pyridaben, tebufenpyrad, tolfenpyrad, flufenerim, cyenopyrafen, cyflumetofen, hydramethylnon, acequinocyl or fluacrypyrim; A19) voltage-dependent sodium channel blockers such as indoxacarb and metaflumizone; A20) inhibitors of the lipid synthesis such as spirodiclofen, spiromesifen and spirotetramat; A21) ryanodine receptor-modulators from the class of diamides consisting of flubendiamide, the phthalamide compounds (R)-3-Chlor-N1-{2-methyl-4-[1,2,2,2-tetrafluor-1-(trifluormethyl)ethyl]phenyl}-N2-(1-methyl-2-methylsulfonylethyl)phthalamid and (S)-3-Chlor-N1-{2-methyl-4-[1,2,2,2-tetrafluor-1-(trifluormethyl)ethyl]phenyl}-N2-(1-methyl-2-methylsulfonylethyl)phthalamid, chloranthraniliprole and cyanthraniliprole; A22) compounds of unknown or uncertain mode of action such as azadirachtin, amidoflumet, bifenazate, fluensulfone, piperonyl butoxide, pyridalyl, sulfoxaflor; or A23) sodium channel modulators from the class of pyrethroids consisting of acrinathrin, allethrin, bifenthrin, cyfluthrin, lambda-cyhalothrin, cypermethrin, alpha-cypermethrin, beta-cypermethrin, zeta-cypermethrin, deltamethrin, esfenvalerate, etofenprox, fenpropathrin, fenvalerate, flucythrinate, tau-fluvalinate, permethrin, silafluofen and tralomethrin.

Fungicides: B1) azoles selected from the group consisting of bitertanol, bromuconazole, cyproconazole, difenoconazole, diniconazole, enilconazole, epoxiconazole, fluquinconazole, fenbuconazole, flusilazole, flutriafol, hexaconazole, imibenconazole, ipconazole, metconazole, myclobutanil, penconazole, propiconazole, prothioconazole, simeconazole, triadimefon, triadimenol, tebuconazole, tetraconazole, triticonazole, prochloraz, pefurazoate, imazalil, triflumizole, cyazofamid, benomyl, carbendazim, thia-bendazole, fuberidazole, ethaboxam, etridiazole and hymexazole, azaconazole, diniconazole-M, oxpoconazol, paclobutrazol, uniconazol, 1-(4-chlorophenyl)-2-([1,2,4]triazol-1-yl)-cycloheptanol and imazalilsulfphate; B2) strobilurins selected from the group consisting of azoxystrobin, dimoxystrobin, enestroburin, fluoxastrobin, kresoximmethyl, methominostrobin, orysastrobin, picoxystrobin, pyraclostrobin, trifloxystrobin, enestroburin, methyl (2-chloro-5-[1-(3-methylbenzyloxyimino)ethyl]benzyl)carbamate, methyl (2-chloro-5-[1-(6-methylpyridin-2-ylmethoxyimino)ethyl]benzyl)carbamate and methyl 2-(ortho-(2,5-dimethylphenyloxymethylene)-phenyl)-3-methoxyacrylate, 2-(2-(6-(3-chloro-2-methyl-phenoxy)-5-fluoro-pyrimidin-4-yloxy)-phenyl)-2-methoxyimino-N-methyl-acetamide and 3-methoxy-2-(2-(N-(4-methoxyphenyl)-cyclopropanecarboximidoylsulfanylmethyl)-phenyl)-acrylic acid methyl ester; B3) carboxamides selected from the group consisting of carboxin, benalaxyl, benalaxyl-M, fenhexamid, flutolanil, furametpyr, mepronil, metalaxyl, mefenoxam, ofurace, oxadixyl, oxycarboxin, penthiopyrad, isopyrazam, thifluzamide, tiadinil, 3,4-dichloro-N-(2-cyanophenyl)isothiazole-5-carboxamide, dimethomorph, flumorph, flumetover, fluopicolide (picobenzamid), zoxamide, carpropamid, diclocymet, mandipropamid, N-(2-(4-[3-(4-chlorophenyl)prop-2-ynyloxy]-3-methoxyphenyl)ethyl)-2-methanesulfonyl-amino-3-methylbutyramide, N-(2-(4-[3-(4-chlorophenyl)prop-2-ynyloxy]-3-methoxy-phenyl)ethyl)-2-ethanesulfonylamino-3-methylbutyramide, methyl 3-(4-chlorophenyl)-3-(2-isopropoxycarbonyl-amino-3-methyl-butyryl amino) propionate, N-(4'-bromobiphenyl-2-yl)-4-difluoromethyl-methylthiazole-δ-carboxamide, N-(4'-trifluoromethyl-biphenyl-2-yl)-4-difluoromethyl-2-methylthiazole-5-carboxamide, N-(4'-chloro-3'-fluorobiphenyl-2-yl)-4-difluoromethyl-2-methyl-thiazole-5-carboxamide, N-(3,4'-dichloro-4-fluorobiphenyl-2-yl)-3-difluoro-methyl-1-methyl-pyrazole-4-carboxamide, N-(3',4'-dichloro-5-fluorobiphenyl-2-yl)-3-difluoromethyl-1-methylpyrazole-4-carboxamide, N-(2-cyano-phenyl)-3,4-dichloroisothiazole-5-carboxamide, 2-amino-4-methyl-thiazole-5-carboxanilide, 2-chloro-N-(1,1,3-trimethyl-indan-4-yl)-nicotinamide, N-(2-(1,3-dimethylbutyl)-phenyl)-1,3-dimethyl-5-fluoro-1H-pyrazole-4-carboxamide, N-(4'-chloro-3',5-difluoro-biphenyl-2-yl)-3-difluoromethyl-1-methyl-1H-pyrazole-4-carboxamide, N-(4'-chloro-3',5-difluoro-biphenyl-2-yl)-3-trifluoromethyl-1-methyl-1H-pyrazole-4-carboxamide, N-(3',4'-dichloro-5-fluoro-biphenyl-2-yl)-3-trifluoromethyl-1-methyl-1H-pyrazole-4-carboxamide, N-(3',5-difluoro-4'-methyl-biphenyl-2-yl)-3-difluoromethyl-1-methyl-1H-pyrazole-4-carboxamide, N-(3',5-difluoro-4'-methyl-biphenyl-2-yl)-3-trifluoromethyl-1-methyl-1H-pyrazole-4-carboxamide, N-(cis-2-bicyclopropyl-2-yl-phenyl)-3-difluoromethyl-1-methyl-1H-pyrazole-4-carboxamide, N-(trans-2-bicyclopropyl-2-yl-phenyl)-3-difluoro-methyl-1-methyl-1H-pyrazole-4-carboxamide, fluopyram, N-(3-ethyl-3,5-5-trimethyl-cyclohexyl)-3-formylamino-2-hydroxy-benzamide, oxytetracyclin, silthiofam, N-(6-methoxy-pyridin-3-yl) cyclopropanecarboxamide, 2-iodo-N-phenyl-benzamide, N-(2-bicyclo-propyl-2-yl-phenyl)-3-difluormethyl-1-methylpyrazol-4-ylcarboxamide, N-(3',4',5'-trifluorobiphenyl-2-yl)-1,3-dimethylpyrazol-4-ylcarboxamide, N-(3',4',5'-trifluorobiphenyl-2-yl)-1,3-dimethyl-5-fluoropyrazol-4-ylcarboxamide, N-(3',4',5'-trifluorobiphenyl-2-yl)-5-chloro-1,3-dimethylpyrazol-4-ylcarboxamide, N-(3',4',5'-trifluorobiphenyl-2-yl)-3-fluoromethyl-1-methylpyrazol-4-ylcarboxamide, N-(3',4',5'-trifluorobiphenyl-2-yl)-3-(chlorofluoromethyl)-1-methylpyrazol-4-ylcarboxamide, N-(3',4',5'-trifluorobiphenyl-2-yl)-3-difluoromethyl-1-methylpyrazol-4-ylcarboxamide, N-(3',4',5'-tri fluorobiphenyl-2-yl)-3-difluoromethyl-5-fluoro-1-methylpyrazol-4-ylcarboxamide, N-(3',4',5'-trifluorobiphenyl-2-yl)-5-chloro-3-difluoromethyl-1-methylpyrazol-4-ylcarboxamide, N-(3',4',5'-trifluorobiphenyl-2-yl)-3-(chlorodifluoromethyl)-1-methylpyrazol-4-ylcarboxamide, N-(3',4',5'-trifluorobiphenyl-2-yl)-1-methyl-3-trifluoromethylpyrazol-4-ylcarboxamide, N-(3',4',5'-trifluorobiphenyl-2-yl)-5-fluoro-1-methyl-3-trifluoromethylpyrazol-4-ylcarboxamide, N-(3',4',5'-trifluorobiphenyl-2-yl)-5-chloro-1-methyl-3-trifluoromethylpyrazol-4-ylcarboxamide, N-(2',4',5'-trifluorobiphenyl-2-yl)-1,3-dimethylpyrazol-4-ylcarboxamide, N-(2',4',5'-trifluorobiphenyl-2-yl)-1,3-dimethyl-5-fluoropyrazol-4-ylcarboxamide, N-(2',4',5'-trifluorobiphenyl-2-yl)-5-chloro-1,3-dimethylpyrazol-4-ylcarboxamide, N-(2',4',5'-trifluorobiphenyl-2-yl)-3-fluoromethyl-1-methylpyrazol-4-ylcarboxamide, N-(2',4',5'-trifluorobiphenyl-2-yl)-3-(chlorofluoromethyl)-1-methylpyrazol-4-ylcarboxamide, N-(2',4',5'-trifluorobiphenyl-2-yl)-3-difluoromethyl-1-methylpyrazol-4-ylcarboxamide, N-(2',4',5'-trifluorobiphenyl-2-yl)-3-difluoromethyl-5-fluoro-1-methylpyrazol-4-ylcarboxamide, N-(2',4',5'-trifluorobiphenyl-2-yl)-5-chloro-3-difluoromethyl-1-methylpyrazol-4-ylcarboxamide, N-(2',4',5'-trifluorobiphenyl-2-yl)-3-(chlorodifluoromethyl)-1-methylpyrazol-4-ylcarboxamide, N-(2',4',5'-trifluorobiphenyl-2-yl)-1-methyl-3-trifluoromethylpyrazol-4-ylcarboxamide, N-(2',4',5'-trifluorobiphenyl-2-yl)-5-fluoro-1-methyl-3-trifluoromethylpyrazol-4-ylcarboxamide, N-(2',4',5'-trifluorobiphenyl-2-yl)-5-chloro-1-methyl-3-trifluoromethylpyrazol-4-ylcarboxamide, N-(3',4'-dichloro-3-fluorobiphenyl-2-yl)-1-methyl-3-trifluoromethyl-1H-pyrazole-4-carboxamide, N-(3',4'-dichloro-3-fluorobiphenyl-2-yl)-1-methyl-3-difluoromethyl-1H-pyrazole-4-carboxamide, N-(3',4'-difluoro-3-fluorobiphenyl-2-yl)-1-methyl-3-trifluoromethyl-1H-pyrazole-4-carboxamide, N-(3',4'-difluoro-3-fluorobiphenyl-2-yl)-1-methyl-S-difluoromethyl-1H-pyrazole-4-carboxamide, N-(3'-chloro-4'-fluoro-3-fluorobiphenyl-2-yl)-1-methyl-3-difluoromethyl-1H-pyrazole-4-carboxamide, N-(3',4'-dichloro-4-fluorobiphenyl-2-yl)-1-methyl-3-trifluoromethyl-1H-pyrazole-4-carboxamide, N-(3',4'-difluoro-4-fluorobiphenyl-2-yl)-1-methyl-S-trifluoromethyl-1H-pyrazole-4-carboxamide, N-(3',4'-dichloro-4-fluorobiphenyl-2-yl)-1-methyl-3-difluoromethyl-1H-pyrazole-4-carboxamide, N-(3',4'-difluoro-4-fluorobiphenyl-2-yl)-1-methyl-3-difluoromethyl-1H-pyrazole-4-carboxamide, N-(3'-chloro-4'-fluoro-4-fluorobiphenyl-2-yl)-1-methyl-S-difluoromethyl-1H-pyrazole-4-carboxamide, N-(3',4'-dichloro-5-fluorobiphenyl-2-yl)-1-methyl-3-trifluoromethyl-1H-pyrazole-4-carboxamide, N-(3',4'-difluoro-5-fluorobiphenyl-2-yl)-1-methyl-3-trifluoromethyl-1H-pyrazole-4-carboxamide, N-(3',4'-dichloro-5-fluorobiphenyl-2-yl)-1-methyl-S-difluoromethyl-1H-pyrazole-4-carboxamide, N-(3',4'-difluoro-5-fluorobiphenyl-2-yl)-1-methyl-3-difluoromethyl-1H-pyrazole-4-carboxamide, N-(3',4'-dichloro-5-fluorobiphenyl-2-yl)-1,3-dimethyl-1H-pyrazole-4-carboxamide, N-(3'-chloro-4'-fluoro-5-fluorobiphenyl-2-yl)-1-methyl-3-difluoromethyl-1H-pyrazole-4-carboxamide, N-(4'-fluoro-4-fluorobiphenyl-2-yl)-1-methyl-3-trifluoromethyl-1H-pyrazole-4-carboxamide, N-(4'-fluoro-5-fluorobiphenyl-2-yl)-1-methyl-3-trifluoromethyl-1H-pyrazole-4-carboxamide, N-(4'-chloro-5-fluorobiphenyl-2-yl)-1-methyl-3-trifluoromethyl-1H-pyrazole-4-carboxamide, N-(4'-methyl-5-fluorobiphenyl-2-yl)-1-methyl-3-trifluoromethyl-1H-pyrazole-4-carboxamide, N-(4'-fluoro-5-fluorobiphenyl-2-yl)-1,3-dimethyl-1H-pyrazole-4-carboxamide, N-(4'-chloro-5-fluorobiphenyl-2-yl)-1,3-dimethyl-1H-pyrazole-4-carboxamide, N-(4'-methyl-5-fluorobiphenyl-2-yl)-1,3-dimethyl-1H-pyrazole-4-carboxamide, N-(4'-fluoro-6-fluorobiphenyl-2-yl)-1-methyl-3-trifluoromethyl-1H-pyrazole-4-carboxamide, N-(4'-chloro-6-fluorobiphenyl-2-yl)-1-methyl-3-trifluoromethyl-1H-pyrazole-4-carboxamide, N-[2-(1,1,2,3,3,3- hexafluoropropoxy)-phenyl]-3-difluoromethyl-1-methyl-1H-pyrazole-4-carboxamide, N-[4'-(trifluoromethylthio)-biphenyl-2-yl]-3-difluoromethyl-1-methyl-1H-pyrazole-4-carboxamide and N-[4'-(trifluoromethylthio)-biphenyl-2-yl]-1-methyl-3-trifluoromethyl-1-methyl-1H-pyrazole-4-carboxamide; B4) heterocyclic compounds selected from the group consisting of fluazinam, pyrifenox, bupirimate, cyprodinil, fenarimol, ferimzone, mepanipyrim, nuarimol, pyrimethanil, triforine, fenpiclonil, fludioxonil, aldimorph, dodemorph, fenpropimorph, tridemorph, fenpropidin, iprodione, procymidone, vinclozolin, famoxadone, fenamidone, octhilinone, proben-azole, 5-chloro-7-(4-methyl-piperidin-1-yl)-6-(2,4,6-trifluorophenyl)-[1,2,4]triazolo[1,5-a]pyrimidine, anilazine, diclomezine, pyroquilon, proquinazid, tricyclazole, 2-butoxy-6-iodo-3-propyl-chromen-4-one, acibenzolar-S-methyl, captafol, captan, dazomet, folpet, fenoxanil, quinoxyfen, N,N-dimethyl-3-(3-bromo-6-fluoro-2-methylindole-1-sulfonyl)-[1,2,4]triazole-1-sulfonamide, 5-ethyl-6-octyl-[1,2,4]triazolo[1,5-a]pyrimidin-2,7-diamine, 2,3,5,6-tetrachloro-4-methanesulfonyl-pyridine, 3,4,5-trichloro-pyridine-2,6-di-carbonitrile, N-(1-(5-bromo-3-chloro-pyridin-2-yl)-ethyl)-2,4-dichloro-nicotinamide, N-((5-bromo-3-chloro pyridin-2-yl)-methyl)-2,4-dichloro-nicotinamide, diflumetorim, nitrapyrin, dodemorphacetate, fluoroimid, blasticidin-S, chinomethionat, debacarb, difenzoquat, difenzoquat-methylsulphate, oxolinic acid and piperalin; B5) carbamates selected from the group consisting of mancozeb, maneb, metam, methasulphocarb, metiram, ferbam, propineb, thiram, zineb, ziram, diethofencarb, iprovalicarb, benthiavalicarb, propamocarb, propamocarb hydrochlorid, 4-fluorophenyl N-(1-(1-(4-cyanophenyl)-ethanesulfonyl)but-2-yl)carbamate, methyl 3-(4-chloro-phenyl)-3-(2-isopropoxycarbonylamino-3-methyl-butyrylamino)propanoate; or B6) other fungicides selected from the group consisting of guanidine, dodine, dodine free base, iminoctadine, guazatine, antibiotics: kasugamycin, streptomycin, polyoxin, validamycin A, nitrophenyl derivatives: binapacryl, dinocap, dinobuton, sulfur-containing heterocyclyl compounds: dithianon, isoprothiolane, organometallic compounds: fentin salts, organophosphorus compounds: edifenphos, iprobenfos, fosetyl, fosetyl-aluminum, phosphorous acid and its salts, pyrazophos, tolclofos-methyl, organochlorine compounds: dichlofluanid, flusulfamide, hexachloro-benzene, phthalide, pencycuron, quintozene, thiophanate-methyl, tolylfluanid, others: cyflufenamid, cymoxanil, dimethirimol, ethirimol, furalaxyl, metrafenone and spiroxamine, guazatine-acetate, iminoctadine-triacetate, iminoctadine-tris(albesilate), kasugamycin hydrochloride hydrate, dichlorophen, pentachlorophenol and its salts, N-(4-chloro-2-nitro-phenyl)-N-ethyl-4-methyl-benzenesulfonamide, dicloran, nitrothal-isopropyl, tecnazen, biphenyl, bronopol, diphenylamine, mildiomycin, oxincopper, prohexadione calcium, N-(cyclopropylmethoxyimino-(6-difluoromethoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluormethyl-4-(3-trimethyl silanyl-propoxy)-phenyl)-N-ethyl-N-methylformamidine and N'-(5-difluormethyl-2-methyl-4-(3-trimethylsilanyl-propoxy)-phenyl)-N-ethyl-N-methyl formamidine.

Herbicides: C1)acetyl-CoA carboxylase inhibitors (ACC), for example cyclohexenone oxime ethers, such as alloxydim, clethodim, cloproxydim, cycloxydim, sethoxydim, tralkoxydim, butroxydim, clefoxydim or tepraloxydim; phenoxyphenoxypropionic esters, such as clodinafop-propargyl, cyhalofop-butyl, diclofop-methyl, fenoxaprop-ethyl, fenoxaprop-P-ethyl, fenthiapropethyl, fluazifop-butyl, fluazifop-P-butyl, haloxyfop-ethoxyethyl, haloxyfop-methyl, haloxyfop-P-methyl, isoxapyrifop, propaquizafop, quizalofop-ethyl, quizalofop-P-ethyl or quizalofop-tefuryl; or arylaminopropionic acids, such as flamprop-methyl or flamprop-isopropyl; C2 acetolactate synthase inhibitors (ALS), for example imidazolinones, such as imazapyr, imazaquin, imazamethabenz-methyl (imazame), imazamox, imazapic or imazethapyr; pyrimidyl ethers, such as pyrithiobac-acid, pyrithiobac-sodium, bispyribac-sodium. KIH-6127 or pyribenzoxym; sulfonamides, such as florasulam, flumetsulam or metosulam; or sulfonylureas, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, halosulfuron-methyl, imazosulfuron, metsulfuron-methyl, nicosulfuron, primisulfuron-methyl, prosulfuron, pyrazosulfuron-ethyl, rimsulfuron, sulfometuron-methyl, thifensulfuron-methyl, triasulfuron, tribenuron-methyl, triflusulfuron-methyl, tritosulfuron, sulfosulfuron, foramsulfuron or iodosulfuron; C3) amides, for example allidochlor (CDAA), benzoylpropethyl, bromobutide, chlorthiamid. diphenamid, etobenzanid, fluthiamide, fosamin or monalide; C4) auxin herbicides, for example pyridinecarboxylic acids, such as clopyralid or picloram; or 2,4-D or benazolin; C5) auxin transport inhibitors, for example naptalame or diflufenzopyr; C6) carotenoid biosynthesis inhibitors, for example benzofenap, clomazone, diflufenican, fluorochloridone, fluridone, pyrazolynate, pyrazoxyfen, isoxaflutole, isoxachlortole, mesotrione, sulcotrione (chlormesulone), ketospiradox, flurtamone, norflurazon or amitrol; C7) enolpyruvylshikimate-3-phosphate synthase inhibitors (EPSPS), for example glyphosate or sulfosate; C8) glutamine synthetase inhibitors, for example bilanafos or glufosinate-ammonium; C9) lipid biosynthesis inhibitors, for example anilides, such as anilofos or mefenacet; chloroacetanilides, such as dimethenamid, S-dimethenamid, acetochlor, alachlor, butachlor, butenachlor, diethatyl-ethyl, dimethachlor, metazachlor, metolachlor, S-metolachlor, pretilachlor, propachlor, prynachlor, terbuchlor, thenylchlor or xylachlor; thioureas, such as butylate, cycloate, di-allate, dimepiperate, EPTC. esprocarb, molinate, pebulate, prosulfocarb, thiobencarb (benthiocarb), tri-allate or vemolate; or benfuresate or perfluidone; C10) mitosis inhibitors, for example carbamates, such as asulam, carbetamid, chlorpropham, orbencarb, propyzamid, propham or tiocarbazil; dinitroanilines, such as benefin, butralin, dinitramin, ethalfluralin, fluchloralin, oryzalin, pendimethalin, prodiamine or trifluralin; pyridines, such as dithiopyr or thiazopyr; or butamifos, chlorthal-dimethyl (DCPA) or maleic hydrazide; C11) protoporphyrinogen IX oxidase inhibitors, for example diphenyl ethers, such as acifluorfen, acifluorfen-sodium, aclonifen, bifenox, chlomitrofen (CNP), ethoxyfen, fluorodifen, fluoroglycofen-ethyl, fomesafen, furyloxyfen, lactofen, nitrofen, nitrofluorfen or oxyfluorfen; oxadiazoles, such as oxadiargyl or oxadiazon; cyclic imides, such as azafenidin, butafenacil, carfentrazone-ethyl, cinidon-ethyl, flumiclorac-pentyl, flumioxazin, flumipropyn, fluropacil, fluthiacet-methyl, sulfentrazone or thidiazimin; or pyrazoles, such as ET-751, JV 485 or nipyraclofen; C12) photosynthesis inhibitors, for example propanil, pyridate or pyridafol; benzothiadiazinones, such as bentazone; dinitrophenols, for example bromofenoxim, dinoseb, dinoseb-acetate, dinoterb or DNOC; dipyridylenes, such as cyperquat-chloride, difenzoquat-methylsulfate, diquat or paraquat-dichloride; ureas, such as chlorbromuron, chlorotoluron, difenoxuron, dimefuron, diuron, ethidimuron, fenuron, fluometuron, isoproturon, isouron, linuron, methabenzthiazuron, methazole, metobenzuron, metoxuron, monolinuron, neburon, siduron or tebuthiuron; phenols, such as bromoxynil or ioxynil; chloridazon; triazines, such as ametryn, atrazine, cyanazine, desmein, dimethamethryn, hexazinone, prometon, prometryn, propazine, simazine, simetryn, terbumeton, terbutryn, terbutylazine or trietazine; triazinones, such as metamitron or metribuzin; uracils, such as bromacil, lenacil or terbacil; or biscarbamates, such as desmedipham or phenmedipham; C13) synergists, for example oxiranes, such as tridiphane; C14) CIS cell wall synthesis inhibitors, for example isoxaben or dichlobenil; C16) various other herbicides, for example dichloropropionic acids, such as dalapon; dihydrobenzofurans, such as ethofumesate; phenylacetic acids, such as chlorfenac (fenac); or aziprotryn, barban, bensulide, benzthiazuron, benzofluor, buminafos, buthidazole, buturon, cafenstrole, chlorbufam, chlorfenprop-methyl, chloroxuron, cinmethylin, cumyluron, cycluron, cyprazine, cyprazole, dibenzyluron, dipropetryn, dymron, eglinazin-ethyl, endothall, ethiozin, flucabazone, fluorbentranil, flupoxam, isocarbamid, isopropalin, karbutilate, mefluidide, monuron, napropamide, napropanilide, nitralin, oxaciclomefone, phenisopham, piperophos, procyazine, profluralin, pyributicarb, secbumeton, sulfallate (CDEC), terbucarb, triaziflam, triazofenamid or trimeturon; or their environmentally compatible salts.

Plant Growth Regulators: D1) Antiauxins, such as clofibric acid, 2,3,5-tri-iodobenzoic acid; D2) Auxins such as 4-CPA, 2,4-D, 2,4-DB, 2,4-DEP, dichlorprop, fenoprop, IAA,IBA, naphthaleneacetamide, α-naphthaleneacetic acids, 1-naphthol, naphthoxyacetic acids, potassium naphthenate, sodium naphthenate, 2,4,5-T; D3) cytokinins, such as 2iP, benzyladenine, 4-hydroxyphenethyl alcohol, kinetin, zeatin; D4) defoliants, such as calcium cyanamide, dimethipin, endothal, ethephon, merphos, metoxuron, pentachlorophenol, thidiazuron, tribufos; D5) ethylene inhibitors, such as aviglycine, 1-methylcyclopropene; D6) ethylene releasers, such as ACC, etacelasil, ethephon, glyoxime; D7) gametocides, such as fenridazon, maleic hydrazide; D8) gibberellins, such as gibberellins, gibberellic acid; D9) growth inhibitors, such as abscisic acid, ancymidol, butralin, carbaryl, chlorphonium, chlorpropham, dikegulac, flumetralin, fluoridamid, fosamine, glyphosine, isopyrimol, jasmonic acid, maleic hydrazide, mepiquat, piproctanyl, prohydrojasmon, propham, tiaojiean, 2,3,5-tri-iodobenzoic acid; D10) morphactins, such as chlorfluren, chlorflurenol, dichlorflurenol, flurenol; D11) growth retardants, such as chlormequat, daminozide, flurprimidol, mefluidide, paclobutrazol, tetcyclacis, uniconazole; D12) growth stimulators, such as brassinolide, brassinolide-ethyl, DCPTA, forchlorfenuron, hymexazol, prosuler, triacontanol; D13) unclassified plant growth regulators, such as bachmedesh, benzofluor, buminafos, carvone, choline chloride, ciobutide, clofencet, cyanamide, cyclanilide, cycloheximide, cyprosulfamide, epocholeone, ethychlozate, ethylene, fuphenthiourea, furalane, heptopargil, holosulf, inabenfide, karetazan, lead arsenate, methasulfocarb, prohexadione, pydanon, sintofen, triapenthenol, trinexapac.

The compositions of the present disclosure can also include a preservative. Suitable preservatives include but are not limited to $C_{12}$ to $C_{15}$ alkyl benzoates, alkyl p-hydroxybenzoates, aloe vera extract, ascorbic acid, benzalkonium chloride, benzoic acid, benzoic acid esters of $C_9$ to $C_{15}$ alcohols, butylated hydroxytoluene, butylated hydroxyanisole, tert-butylhydroquinone, castor oil, cetyl alcohols, chloro cresol, citric acid, cocoa butter, coconut oil, diazolidinyl urea, diisopropyl adipate, dimethyl polysiloxane, DMDM hydantoin, ethanol, ethylenediaminetetraacetic acid, fatty acids, fatty alcohols, hexadecyl alcohol, hydroxybenzoate esters, iodopropynyl butylcarbamate, isononyl isononanoate, jojoba oil, lanolin oil, mineral oil, oleic acid, olive oil, parabens, polyethers, polyoxypropylene butyl ether, polyoxypropylene cetyl ether, potassium sorbate, propyl gallate, silicone oils, sodium propionate, sodium benzoate, sodium bisulfite, sorbic acid, stearic fatty acid, sulfur dioxide, vitamin E, vitamin E acetate and derivatives, esters, salts and mixtures thereof. Preferred preservatives include sodium o-phenylphenate, 5-chloro-2-methyl-4-isothiazolin-3-one, 2-methyl-4-isothiazolin-3-one, and 1,2-benisothiazolin-3-one.

In one preferred embodiment, the additional crop protection agent is atrazine. Increased herbicidal activity was observed when atrazine was added to the composition of Example 2, vide infra, in control of ivyleaf morningglory, waterhemp, giant foxtail, green foxtail and giant ragweed. The herbicidal activity of the compositions of this disclosure can be used to control herbicide-resistant weeds, such as glyphosate-resistant weeds, including glyphosate-resistant waterhemp.

DEFINITIONS

As used in this application and unless otherwise indicated the term "herbicide" refers to a compositional mixture that is produced, sold, or used in a field in order to kill or otherwise inhibit unwanted plants such as, but not limited to, deleterious or annoying weeds, broadleaf plants, grasses, and sedges; and can be used for crop protection, edifice protection or turf protection. The term "herbicide" includes the end-use herbicidal product. This composition can be a pure compound, a solution of chemical compounds, a mixture of chemical compounds, an emulsion, a suspension, a solid-liquid mixture, or a liquid-liquid mixture. The term "herbicide" also refers to the product that passes through the commercial channels from the manufacturer to the ultimate end user who can either apply the herbicide to the affected field as sold, or mix it with other excipients.

The term "weed" means and includes any plant which grows where not wanted.

The term "herbicidally effective amount" means an amount necessary to produce an observable herbicidal effect on unwanted plant growth, including one or more of the effects of necrosis, death, growth inhibition, reproduction inhibition, inhibition of proliferation, and removal, destruction, or otherwise diminishing the occurrence and activity of unwanted plants.

The term "herbicidally active ingredient" means the active ingredient in the herbicide that causes the herbicide to prevent, destroy, repel or mitigate any weed. Other ingredients of the herbicide that are not herbicidally active ingredients are excipients that aid in forming, storing, or delivering herbicidally active ingredient to the target. Examples of excipients in the present embodiment include, without limitation, an organic liquid in which herbicidally active ingredient is dissolved, a polyurea shell, a water-soluble polymer, and one or more salts.

The definition of the term "herbicidal composition" refers to a herbicide, and in addition, to any composition that comprises a herbicidally active ingredient. This composition can be a solution or a mixture. Further, the definition of the term "herbicidal composition" also refers to a product intended for use in manufacruting, or any product intended for formulation or repackaging into other agricultural products.

"Fluthiacet-methyl" is the common name for methyl [[2-chloro-4-fluoro-5-[(tetrahydro-3-oxo-1H,3H-[1,3,4] thiadiazolo [3,4-a]pyridazin-1-ylidene)amino]phenyl]thio] acetate.

"HPPD inhibitor" means a compound that inhibits para-hydroxyphenylpyruvate dioxygenase.

The following examples serve only to illustrate the invention and should not be interpreted as limiting the scope of the invention in any way, since further modifications encompassed by the disclosed invention will be apparent to those skilled in the art. All such modifications are deemed to be within the scope of the invention as defined in the present specification and claims.

EXAMPLES

Example 1

SC Formulation of Fluthiacet-methyl and Mesotrione, 1:17.5 Ratio by Weight

A mixture of 51.8 grams of magnesium aluminum silicate (VEEGUM® Ultra, available from Vanderbuilt Minerals LLC) in 3,077.0 grams of deionized water was stirred vigorously for about one hour at room temperature. To this was added 511.8 grams of propylene glycol, 10.8 grams of an antifoam agent (Dow Corning® AF Emulsion, available from Dow Corning Corporation), 204.9 grams of a wetting agent (Morwet D-425® Powder, available from AkzoNobel Agrochemicals), 257.0 grams of premelted polyalkylene oxide block copolymer (Atlas™ G-5000, available from Croda Crop Care) and 256.7 grams of an acrylic graft copolymer (Atlox® 491, available from Croda Crop Care). The mixture was stirred until uniform. Technical grade mesotrione (5,594.0 grams, 83.0% purity) and fluthiacet-methyl (273 grams, 97.5% purity) were added and the mixture milled at a temperature of about 35° C. to about 45° C. until a particle size of less than 3 microns was achieved. The milled mixture was transferred to a tank fixed with a stirring blade. The mill tank was rinsed with about 170 grams of deionized water and the rinse added to the milled mixture. To this was added 1,080.0 grams of an aqueous mixture containing 2% by weight xanthan gum and 1.3% by weight biocide (Kathon™ Preserative, available from Dow Chemical Company). This was stirred for four hours at which time the pH was adjusted to 4.62 by adding 10.3 grams of triethanolamine. An additional 171.0 grams of deionized water was added and the mixture stirred until homogenous. Analysis of this mixture indicated it contained 38.4% by weight mesotrione, 2.22% by weight fluthiacet-methyl with an average particle size of 1.63(D90) and a density of 1.18 gm/mL.

Example 2

SC Formulation of Fluthiacet-methyl and Mesotrione, 1:32.5 Ratio by Weight

A mixture of 72.8 grams of magnesium aluminum silicate (VEEGUM® Ultra, available from Vanderbuilt Minerals LLC) in 4,369.3 grams of deionized water was stirred vigorously for about one hour at room temperature. To this was added 728.2 grams of propylene glycol, 14.6 grams of an antifoam agent (Dow Corning® AF Emulsion, available from Dow Corning Corporation), 291.3 grams of a wetting agent (Morwet D-425® Powder, available from AkzoNobel Agrochemicals), 364.1 grams of premelted polyalkylene oxide block copolymer (Atlas™ G-5000, available from Croda Crop Care) and 364.1 grams of an acrylic graft copolymer (Atlox® 491, available from Croda Crop Care). The mixture was stirred until uniform. Technical grade mesotrione (4,499.8 grams, 83.0% purity) and fluthiacet-methyl (119.5 grams, 97.5% purity) were added and the mixture milled at a temperature of about 35° C. to about 45° C. until a particle size of less than 3 microns was achieved. The milled mixture was transferred to a tank fixed with a stirring blade. The mill tank was rinsed with 1324.0 grams of deionized water and the rinse added to the milled mixture. To this was added 1,243.9 grams of an aqueous mixture containing 2% by weight xanthan gum and 1.3% by weight biocide (Kathon™ Preserative, available from Dow Chemical Company). This was stirred for four hours at which time the pH was adjusted to 4.8 by adding 24.7 grams of triethanolamine. An additional 1324.3 grams of deionized water was added and the mixture stirred until homogenous. Analysis of this mixture indicated it contained 30.6% by weight mesotrione, 0.81% by weight fluthiacet-methyl with an average particle size of 2.31(D90) and a density of 1.14 gm/mL.

Example 3

Post-Emergent Herbicidal Evaluation of Fluthiacet-Methyl in Mixtures with HPPD Herbicides Compositions of the present disclosure were tested for herbicidal efficacy in the following manner:

Test compositions containing Fluthiacet-methyl (Cadet® Herbicide), tembotrione (Laudis® Herbicide), topramezone (Impact® Herbicide), mesotrione (Callisto® Herbicide) and mixtures of fluthiacet-methyl with these HPPD herbicides, were diluted with water to provide the appropriate test rate concentrations. A crop oil concentrate (1% v/v, crop oil concentrate, COC, or methylated seed oil, MSO) was added to each test solution.

The test crop was Pioneer 33M53 corn and the test weeds were redroot pigweed (*Amaranthus etoflexus*), morningglory (*Ipamea* spp) and common waterhemp (*Amaranthus rudis*).

For post-emergence testing, three disposable 3 inch square pots for each rate of application of each herbicide solution were filled with a soil, comprised of peat moss, vermiculite, bark ash, pine bark, limestone and a wetting agent (Metro Mix 360 artificial soil, Scotts Company, Marysville, Ohio), to which 8 to 10 seeds were planted. The pots were placed in a greenhouse and watered daily, thus allowing the seeds to germinate and the foliage to develop into 5 inch to 6 inch plants.

Pots designated for treatment were placed on a conveyor belt and the conveyor belt fed under a spray nozzle mounted about ten inches above the post-emergent foliage. The spray of herbicidal solution was commenced and once stabilized; the pots were passed under the spray at a speed to receive a coverage equivalent of 30 gallons per acre. The application rates are those shown in Table 1 below for the individual herbicidal solutions and the herbicide compositions of the present disclosure. The post-emergence pots were immediately placed in the green-house and not watered for 24 hours after treatment. Thereafter they were regularly watered at ground level. The control of weeds was evaluated in each experimental test at 21 days after treatment (DAT). The results after 21 days, shown as an average of the replications, were compared with results observed in untreated control pots in the same tests. The results are in Table 1 below. Test mixtures of fluthiacet-methyl-methyl and HPPD herbicides were found to exhibit similar or less crop injury then the individually applied herbicides when applied to field corn.

Percent control was determined by a method similar to the 0 to 100 rating system disclosed in "Research Methods in Weed Science," 2nd ed., B. Truelove, Ed.; Southern Weed Science Society; Auburn University, Auburn, Ala., 1977. The rating system is as follows:

Herbicide Rating System

| Rating Percent Control | Description of Main Categories | Weed Description |
|---|---|---|
| 0 | No Effect | No weed control |
| 10 | | Very poor weed control |
| 20 | Slight Effect | Poor weed control |
| 30 | | Poor to deficient weed control |
| 40 | | Deficient weed control |
| 50 | Moderate Effect | Deficient to moderate weed control |
| 60 | | Moderate weed control |
| 70 | | Control somewhat less than satisfactory |
| 80 | Severe | Satisfactory to good weed control |
| 90 | | Very good to excellent weed control |
| 100 | Complete Effect | Complete weed destruction | lation of Example 2 were diluted with water to provide the appropriate test rate concentrations.

The test weeds include purple nutsedge (*Cyperus rotundus*, PN), Egyptian crowfoot grass (*Dactylocatenium aegyptim*, ECG), fumitory (*Fumaria indica*, FUM), giant pigweed (*Trianthema protulacastrum*, GPW), lambsquarters (*Chenopodium album*, LQ), denticulate medick (*Medacigo denticulate*, DM), lesser swine cress (*Coronopus dodymus*, LSC), brown beetle grass (*Diplachne fusca*, BBG), jungle grass (*Echinochloa colonum*, JG), tendla (*Digera arvensis*, TEN), and field bindweed (*Convolvulus arvensis*, FBW).

The test compositions were sprayed on 800 to 1000 square foot test plots (9 replicates at 3 sites in India, one in Lahore and two in) using a back pack sprayer at a rate of 188 liters per hectare when the crop (grain hybrid corn) and weeds were at the 4 to 5 leaf growth stage. The percent phytotoxicity to corn (discoloration of leaves and miss-shaped leaves) was determined at 10 days after treatment (DAT) and the percent control of weeds was determined at 45 DAT. Table 2 below summarizes this data. The untreated control plots had no damage to the corn and no control of weeds.

The expected phytotoxicity to corn and the expected control of weeds is calculated using the Colby Equation (S.

TABLE 1

Percent Control of Weeds Using Mixtures of Fluthiacet-methyl and HPPD Herbicides 21 Days After Treatment (DAT) (Four replications)

| Treatment | Rate of Application Gm Ai/HA | % Visual Corn Injury 14 DAT | % Control of Weeds | | |
|---|---|---|---|---|---|
| | | | Red Root Pigweed | Common Waterhemp | Morningglory |
| Non-Treated Control | 0 | 0 | 0 | 0 | 0 |
| Ex 1 + COC[1] | 52.6 | 1 | 80 | 97 | 100 |
| Ex 1 + COC | 75.0 | 4 | 75 | 99 | 100 |
| Ex 1 + COC | 109.0 | 6 | 85 | 100 | 100 |
| Cadet ® + Laudis ® + MSO[2] | 2.9 + 45.9 | 4 | 81 | 97 | 100 |
| Cadet ® + Laudis ® + MSO | 4.0 + 91.8 | 4 | 83 | 100 | 100 |
| Cadet ® + Laudis ® + MSO | 5.9 + 153.0 | 4 | 86 | 100 | 100 |
| Cadet ® + Impact ® + COC | 2.9 + 6.1 | 5 | 60 | 93 | 100 |
| Cadet ® + Impact ® + COC | 4.0 + 12.2 | 6 | 75 | 99 | 100 |
| Cadet ® + Impact ® + COC | 5.9 + 24.5 | 9 | 79 | 100 | 100 |
| Cadet ® + COC | 2.9 | 3 | 61 | 79 | 100 |
| Cadet ® + COC | 4.0 | 8 | 58 | 76 | 100 |
| Cadet ® + COC | 5.9 | 6 | 74 | 73 | 100 |
| Laudis ® + MSO | 45.9 | 3 | 41 | 84 | 85 |
| Laudis ® + MSO | 91.8 | 4 | 46 | 93 | 95 |
| Laudis ® + MSO | 153.0 | 8 | 34 | 95 | 85 |
| Impact ® + COC | 6.2 | 4 | 34 | 91 | 86 |
| Impact ® + COC | 12.2 | 6 | 36 | 91 | 84 |
| Impact ® + COC | 24.5 | 5 | 35 | 99 | 96 |
| Callisto ® + COC | 49.7 | 5 | 31 | 93 | 91 |
| Callisto ® + COC | 70.0 | 2 | 29 | 92 | 94 |
| Callisto ® + COC | 105.0 | 5 | 29 | 92 | 95 |

[1]crop oil concentrate (COC) added, 1% by volume
[2]methylated seed oil (MSO) added, 1% by volume Example 4

Post-emergence Control of Weeds Using Fluthiacet-methyl and Mesotrione

Compositions of the present disclosure were tested for herbicidal efficacy in the following manner:

Test compositions containing Fluthiacet-methyl (Cadet® Herbicide), mesotrione (15% SC formulation), mixtures of Cadet® Herbicide and mesotrione 15% SC, and the formu- R. Colby, Weeds, Vol. 15, No. 1, pgs 20-22, 1967) and is also provide in the table below. The Expected value "E" is calculated using the following equation; $E = X + Y - (XY/100)$; where X is the observed control of the first active at rate x1 and Y is the observed control of the second active at rate y1. When the observed response of the combination is greater than the expected, the combination is synergistic; when less than expected, it is antagonistic; when the observed and expected are the same, the combination is additive.

TABLE 2

Post-emergence Control of Weeds In Corn Crop

% Phytotoxicity to Corn and % Control of Weeds

| Plant Species | Cadet ® at 5.0 Gm/Ha | Mesotrione at 185 Gm/Ha | Expected Value | Ex 2 at 5.0 + 183.4 Gm/Ha | Cadet ® at 5.0 Gm/Ha + mesotrione at 185 Gm/Ha Tank Mix |
|---|---|---|---|---|---|
| Corn (Phytotoxicity) | 15 | 10 | 23 | 8 | 15 |
| PN | 25 | 30 | 48 | 88 | 85 |
| ECG | 5 | 10 | 15 | 92 | 90 |
| FUM | 40 | 80 | 88 | 96 | 95 |
| GPW | 40 | 40 | 64 | 95 | 94 |
| LQ | 20 | 85 | 88 | 98 | 95 |
| DM | 35 | 88 | 92 | 98 | 94 |
| LSC | 50 | 70 | 85 | 98 | 93 |
| BBG | 10 | 40 | 46 | 98 | 90 |
| JG | 0 | 70 | 70 | 95 | 93 |
| TEN | 10 | 60 | 64 | 98 | 94 |
| FBW | 0 | 40 | 40 | 88 | 90 |

Example 5

Weed Control in Sugarcane Field Tests

The composition of Example 2 was tested in sugarcane fields in India for weed control and crop safety. The composition of Example 2 was diluted with water and applied to test plots of 800 to 1000 square foot at five sugarcane farm locations. The composition was applied at a rate of 400, 500 and 600 mL of test composition per acre as pre-emergence and early post-emergence applications (15 days after sowing) using backpack sprayers. A pre-emergent standard, Metric® Herbicide (clomazone and metribuzin) and a post-emergent standard, Flisto Gold® Herbicide (atrazine and mesotrione) were included at 1 liter formulation diluted in water per acre. The data from all 5 trials was averaged and summarized in Table 3 below. Untreated control plots were also included. Data for the pre-emergence trials was collected 20-25 days after application; early post-emergence data was collected 18-20 days after treatment. No damage to sugarcane plants was seen in any of the test plots. Weed species included false amaranth (*Digera muricata*, FA), giant pigweed (*Trianthema portullactastrum*, GPW), Egyptian crowfoot grass (*Dactylium aegyptium*, ECG), purple nutsedge (*Cyperus rotundus*, PN), common purslane (*Portulaca oleracea*, CP) and field bindweed (*Convolvulus arvensis*, FBW).

TABLE 3

Weed Control In Sugarcane Field Plots

| | % Control of Weeds | | | | | |
|---|---|---|---|---|---|---|
| Treatment | FA | GPW | ECG | PN | CP | FBW |
| 400 mL pre-emergence | 90 | 85 | 85 | 90 | 90 | 70 |
| 500 mL pre-emergence | 94 | 93 | 90 | 94 | 95 | 75 |
| 600 mL pre-emergence | 98 | 97 | 94 | 96 | 96 | 78 |
| 400 mL post-emergence | 92 | 90 | 92 | 94 | 92 | 65 |
| 500 mL post-emergence | 96 | 95 | 95 | 95 | 94 | 70 |
| 600 mL post-emergence | 98 | 98 | 97 | 96 | 97 | 70 |
| Metric ® Herbicide 1 Liter pre-emergence | 92 | 90 | 85 | 30 | 93 | 10 |
| Flisto Gold ® Herbicide 1 Liter post-emergence | 85 | 70 | 60 | 30 | 85 | 10 |

As can be seen in the above table, the composition of Example 2 is equal to or in many cases more active than the commercial standards.

Example 6

Control of Palmer Amaranth and Waterhemp with Fluthiacet-Methyl and Mesotrione Compositions Compositions of the present disclosure were tested for herbicidal efficacy in the following manner:

Test compositions containing Fluthiacet-methyl (Cadet® Herbicide), mesotrione (15% SC formulation), mixtures of Cadet® Herbicide and mesotrione 15% SC and the formulation of Example 1 were diluted with water to provide the appropriate test rate concentrations. Test plots in Nebraska, Iowa, Kansas and Illinois were sprayed with the test compositions to determine control of common waterhemp (*Amaranthus rudis*) in corn fields. Test plots in Indiana and Kansas were sprayed with the test compositions to determine palmer amaranth (*Amaranthus palmeri*) control in corn crops. Test plots in Kansas, Illinois and Nebraska were sprayed with the test compositions to determine morning-glory (*Convolvulaceae* sp.) control in corn crops.

Test solutions of the following were prepared: solutions of Example 2 applied at 2.0, 2.5 and 3.15 ounces of the composition per acre, diluted in water; Cadet® Herbicide was applied at 0.6 ounce of the formulation per acre, diluted in water; Callisto® Herbicide applied at 2.37 ounces of the formulation per acre, diluted with water; A mixture of Cadet® Herbicide applied at 0.6 ounce of the formulation per acre, diluted in water and Callisto® Herbicide applied at 2.37 ounces of the formulation per acre, diluted with water; A mixture of Example 2 at 2.5 ounces of the composition and 16 ounces of Atrazine 4L Flowable Herbicide per acre, diluted with water. All test solutions contained 1% v/v crop oil concentrate. The average of the waterhemp evaluations and the palmer amaranth evaluations are summarized in Table 4 below. The addition of atrazine to the composition of Example 2 increases the herbicidal activity substantially.

TABLE 4

Summary of Waterhemp, Palmer Amaranth and Morningglory % Control

| Weed Species | % Control | | | | | | |
|---|---|---|---|---|---|---|---|
| | Ex 1 @ 2 oz | Ex 1 @ 2.5 oz | Ex 1 @ 3.15 oz | Cadet ® + Callisto ® | Cadet ® | Callisto ® | Ex 1 @ 2.5 oz + Atrazine |
| Common Waterhemp | 81 | 86 | 90 | 78 | 52 | 81 | 97 |
| Palmer Amaranth | 92 | 82 | 86 | 87 | 74 | 83 | 95 |
| Morningglory | 79 | 80 | 87 | 70 | 56 | 85 | 95 |

While this invention has been described with an emphasis upon preferred embodiments, it will be obvious to those of ordinary skill in the art that variations in the preferred compositions and methods can be used and that it is intended that the invention can be practiced otherwise than as specifically described herein. Accordingly, this invention includes all modifications encompassed within the spirit and scope of the invention as defined by the claims that follow.

What is claimed is:

1. A method for controlling weeds in a crop, comprising applying to weeds having an average height ranging from about 4 inches to about 8 inches a herbicidally effective amount of a composition comprising (a) fluthiacet-methyl and (b) a p-hydroxyphenylpyruvate dioxygenase (HPPD) inhibitor; and (c) a fungicide selected from the group consisting of: bitertanol, bromuconazole, cyproconazole, difenoconazole, diniconazole, enilconazole, epoxiconazole, fluquinconazole, fenbuconazole, flusilazole, flutriafol, hexaconazole, imibenconazole, ipconazole, metconazole, myclobutanil, penconazole, propiconazole, prothioconazole, simeconazole, triadimefon, triadimenol, tebuconazole, tetraconazole, triticonazole, prochloraz, pefurazoate, imazalil, triflumizole, cyazofamid, benomyl, carbendazim, thia-bendazole, fuberidazole, ethaboxam, etridiazole and hymexazole, azaconazole, diniconazole-M, oxpoconazol, paclobutrazol, uniconazol, 1-(4-chlorophenyl)-2-([1,2,4]triazol-1-yl)-cycloheptanol and imazalilsulfphate, wherein the fluthiacet-methyl and the HPPD inhibitor are present in a ratio between about 1:15 and 1:35, and wherein said ratio provides synergistic control of the weeds.

2. The method of claim 1, wherein the HPPD inhibitor is mesotrione and the fungicide is difenaconazole or prothioconazole.

3. The method of claim 2, wherein the average height of the weeds is from about 4 inches to about 6 inches.

4. The method of claim 2, wherein the weeds comprise one or more selected from the group consisting of: waterhemp, lambsquarters, velvetleaf, palmer amaranth, pigweed, morning glory, cocklebur, ragweed, broadleaf signalgrass, foxtail, crabgrass and volunteer soybean.

5. The method of claim 2, wherein the crop is selected from the group consisting of corn and sugarcane.

6. A method for controlling weeds in a crop, comprising applying to weeds having an average height ranging from about 4 inches to about 8 inches a herbicidally effective amount of a composition comprising (a) fluthiacet-methyl and (b) a p-hydroxyphenylpyruvate dioxygenase (HPPD) inhibitor; and (c) a fungicide selected from the group consisting of: azoxystrobin, dimoxystrobin, enestroburin, fluoxastrobin, kresoxim-methyl, methominostrobin, orysastrobin, picoxystrobin, pyraclostrobin, trifloxystrobin, enestroburin, methyl (2-chloro-5-[1-(3-methylbenzyloxyimino) ethyl]benzyl)carbamate, methyl (2-chloro-5-[1-(6-methylpyridin-2-ylmethoxyimino)ethyl]benzyl)carbamate and methyl 2-(ortho-(2,5-dimethylphenyloxymethylene)-phenyl)-3-methoxyacrylate, 2-(2-(6-(3-chloro-2-methyl-phenoxy)-5-fluoro-pyrimidin-4-yloxy)-phenyl)-2-methoxy-imino-N-methyl-acetamide and 3-methoxy-2-(2-(N-(4-methoxy-phenyl)-cyclopropanecarboximidoylsulfanylmethyl)-phenyl)-acrylic acid methyl ester, wherein the fluthiacet-methyl and the HPPD inhibitor are present in a ratio between about 1:15 and 1:35, and wherein said ratio provides synergistic control of the weeds.

7. The method of claim 6, wherein the fungicide is pyraclostrobin and azoxystrobin.

8. The method of claim 7, wherein the HPPD inhibitor is mesotrione.

9. The method of claim 8, wherein the average height of the weeds is from about 4 inches to about 5 inches or from about 4 inches to about 6 inches.

10. The method of claim 9, wherein the weeds comprise one or more selected from the group consisting of waterhemp, lambsquarters, velvetleaf, palmer amaranth, pigweed, morning glory, cocklebur, ragweed, broadleaf signalgrass, foxtail, crabgrass and volunteer soybean.

11. The method of claim 9, wherein the crop is selected from the group consisting of corn and sugarcane.

12. A method for controlling weeds in a crop, comprising applying to weeds having an average height ranging from about 4 inches to about 8 inches a herbicidally effective amount of a composition comprising (a) fluthiacet-methyl and (b) a p-hydroxyphenylpyruvate dioxygenase (HPPD) inhibitor; and (c) a fungicide selected from the group consisting of: carboxin, benalaxyl, benalaxyl-M, fenhexamid, flutolanil, furametpyr, mepronil, metalaxyl, mefenoxam, ofurace, oxadixyl, oxycarboxin, penthiopyrad, isopyrazam, thifluzamide, tiadinil, 3,4-dichloro-N-(2-cyano-phenyl)isothiazole-5-carboxamide, dimethomorph, flumorph, flumetover, fluopicolide (picobenzamid), zoxamide, carpropamid, diclocymet, mandipropamid, N-(2-(4[3-(4-chlorophenyl)prop-2-ynyloxy]-3-methoxyphenyl)ethyl)-2-methanesulfonyl-amino-3-methylbutyramide, N-(2-(4-[3-(4-chlorophenyl)prop-2-ynyloxy]3-methoxy-phenyl)ethyl)-2-ethanesulfonylamino-3-methylbutyramide, methyl 3-(4-chlorophenyl)-3-(2-isopropoxycarbonyl-amino-3-methyl-butyrylamino)propionate, N-(4'-bromobiphenyl-2-yl)-4-difluoromethyl-methylthiazole-δ-carboxamide, N-(4'-trifluoromethyl-biphenyl-2-yl)-4-difluoromethyl-2-methylthiazole-5-carboxamide, N-(4'-chloro-3'-fluorobiphenyl-2-yl)-4-difluoromethyl-2-methyl-thiazole-5-carboxamide, N-(3,4'-dichloro-4-fluorobiphenyl-2-yl)-3-difluoro-methyl-1-methyl-pyrazole-4-carboxamide, N-(3', 4'-dichloro-5-fluorobiphenyl-2-yl)-3-difluoromethyl-1-methylpyrazole-4-carboxamide, N-(2-cyano-phenyl)-3,4-dichloroisothiazole-5-carboxamide, 2-amino-4-methylthiazole-5-carboxanilide, 2-chloro-N-(1,1,3-trimethyl-indan-4-yl)-nicotinamide, N-(2-(1,3-dimethylbutyl)-phenyl)-1,3-dimethyl-5-fluoro-1 H-pyrazole-4-carboxamide, N-(4'-chloro-3',5-difluoro-biphenyl-2-yl)-3-difluoromethyl-1-methyl-1 H-pyrazole-4-carboxamide, N-(4'-chloro-3',5-difluoro-biphenyl-2-yl)-3-trifluoromethyl-1 -methyl-1H-pyrazole-4-carboxamide, N-(3',4'-dichloro-5-fluorobiphenyl-2-yl)-3-trifluoromethyl-1-methyl-1H-pyrazole-4-carboxamide, N-(3',5-difluoro-4'-methyl-biphenyl-2-yl)-3-difluoromethyl-1-methyl-1H-pyrazole-4-carboxamide, N-(3',5-difluoro-4'-methyl-biphenyl-2-yl)-3-trifluoromethyl-1-methyl-1H-pyrazole-4-carboxamide, N-(cis-2-bicyclopropyl-2-yl-phenyl)-3-difluoromethyl-1-methyl-1H-pyrazole-4-carboxamide, N-(trans-2-bicyclopropyl-2-yl-phenyl)-3-difluoro-methyl-1-methyl-1 H-pyrazole-4-carboxamide, fluopyram, N-(3-ethyl-3,55trimethyl-cyclohexyl)-3-formylamino-2-hydroxy-benzamide, oxytetracyclin, silthiofam, N-(6-methoxy-pyridin-3-yl) cyclopropanecarboxamide, 2-iodo-N-phenyl-benzamide, N-(2-bicyclo-propyl-2-yl -phenyl)-3-difluormethyl-1-methylpyrazol-4-ylcarboxamide, N-(3',4',5'-trifluorobiphenyl-2-yl)-1,3-dimethylpyrazol-4-ylcarboxamide, N-(3',4',5'-trifluorobiphenyl-2-yl)-1,3-dimethyl-5-fluoropyrazol-4-ylcarboxamide, N-(3',4',5'-trifluorobiphenyl-2-yl)-5-chloro-1,3-dimethyl-pyrazol-4-ylcarboxamide, N-(3',4',5'-trifluorobiphenyl-2-yl)-3-fluoromethyl-1-methylpyrazol-4-ylcarboxamide, N-(3',4',5'-trifluorobiphenyl-2-yl)-3-(chlorofluoromethyl)-1-methylpyrazol-4-ylcarboxamide,N-(3',4',5'-trifluorobiphenyl-2-yl)-3-difluoromethyl-1-methylpyrazol-4-ylcarboxamide, N-(3',4',5'-trifluorobiphenyl-2-yl)-3-difluoromethyl-5-fluoro-1-methylpyrazol-4-ylcarboxamide, N-(3',4',5'-trifluorobiphenyl-2-yl)-5-chloro-3-difluoromethyl-1-methylpyrazol-4-ylcarboxamide, N-(3',4',5'-trifluorobiphenyl-2-yl)-3-(chlorodifluoromethyl)-1-methylpyrazol-4-ylcarboxamide, N-(3',4',5'-trifluorobiphenyl-2-yl)-1-methyl-3-trifluoromethylpyrazol-4-ylcarboxamide, N-(3',4',5'-trifluorobiphenyl-2-yl)-5-fluoro-1-methyl-3-trifluoromethylpyrazol-4-ylcarboxamide, N-(3',4',5'-trifluorobiphenyl-2-yl)-5-chloro-1-methyl-3-trifluoromethylpyrazol-4-ylcarboxamide, N-(2',4',5'-trifluorobiphenyl-2-yl)-1,3-dimethylpyrazol-4-ylcarboxamide, N-(2',4',5'-trifluorobiphenyl-2-yl)-1,3-dimethyl-5-fluoropyrazol-4-ylcarboxamide, N-(2',4',5'-trifluorobiphenyl-2-yl)-5-chloro-1,3-dimethylpyrazol-4-ylcarboxamide, N-(2',4',5'-trifluorobiphenyl-2-yl)-3-fluoromethyl-1-methylpyrazol-4-ylcarboxamide, N-(2',4',5'-trifluorobiphenyl-2-yl)-3-(chlorofluoromethyl)-1-methylpyrazol-4-ylcarboxamide, N-(2',4',5'-trifluorobiphenyl-2-yl)-3-difluoromethyl-1-methylpyrazol-4-ylcarboxamide, N-(2',4',5'-trifluorobiphenyl-2-yl)-3-difluoromethyl-5-fluoro-1-methylpyrazol-4-ylcarboxamide, N-(2',4',5'-trifluorobiphenyl-2-y1)-5-chloro-3-difluoromethyl-1-methylpyrazol-4-ylcarboxamide, N-(2',4',5'-trifluorobiphenyl-2-yl)-3-(chlorodifluoromethyl)-1-methylpyrazol-4-ylcarboxamide, N-(2',4',5'-trifluorobiphenyl-2-yl)-1-methyl-3-trifluoromethylpyrazol-4-ylcarboxamide, N-(2',4',5'-trifluorobiphenyl-2-yl)-5-fluoro-1-methyl-3-trifluoromethylpyrazol-4-ylcarboxamide, N-(2',4',5'-trifluorobiphenyl-2-yl)-5-chloro-1-methyl-3-trifluoromethylpyrazol-4-ylcarboxamide, N-(3',4'-dichloro-3-fluorobiphenyl-2-yl)-1-methyl-3-trifluoromethyl-1H-pyrazole-4-carboxamide, N-(3',4'-dichloro-3-fluorobiphenyl-2-yl)-1 -methyl-3-difluoromethyl-1H-pyrazole-4-carboxamide, N-(3',4'-difluoro-3-fluorobiphenyl-2-yl)-1-methyl-3-trifluoromethyl-1H-pyrazole-4-carboxamide, N-(3',4'-difluoro-3-fluorobiphenyl-2-yl)-1-methyl-S-difluoromethyl-1H-pyrazole-4-carboxamide, N-(3'-chloro-4'-fluoro-3-fluorobiphenyl-2-yl)-1-methyl-3-difluoromethyl-1 H-pyrazole-4-carboxamide, N-(3',4'-dichloro-4-fluorobiphenyl-2-yl)-1-methyl-3-trifluoromethyl-1 H-pyrazole-4-carboxamide, N-(3',4'-difluoro-4-fluorobiphenyl-2-yl)-1-methyl-S-trifluoromethyl-1H-pyrazole-4-carboxamide, N-(3',4'-dichloro-4-fluorobiphenyl-2-yl)-1-methyl-3-difluoromethyl-1H-pyrazole-4-carboxamide, N-(3',4'-difluoro-4-fluorobiphenyl-2-yl)-1-methyl-3-difluoromethyl-1H-pyrazole-4-carboxamide, N-(3'-chloro-4'-fluoro-4-fluorobiphenyl-2-yl)-1-methyl-S-difluoromethyl-1H-pyrazole-4-carboxamide, N-(3',4'-dichloro-5-fluorobiphenyl-2-yl)-1-methyl-3-trifluoromethyl-1H-pyrazole-4-carboxamide, N-(3',4'-difluoro-5-fluorobiphenyl-2-yl)-1-methyl-3-trifluoromethyl-1H-pyrazole-4-carboxamide, N-(3',4'-dichloro-5-fluorobiphenyl-2-yl)-1-methyl-S-difluoromethyl-1H-pyrazole-4-carboxamide, N-(3',4'-difluoro-5-fluorobiphenyl-2-yl)-1-methyl-3-difluoromethyl-1H-pyrazole-4-carboxamide, N-(3',4'-dichloro-5-fluorobiphenyl-2-yl)-1,3-dimethyl-1H-pyrazole-4-carboxamide, N-(3'-chloro-4'-fluoro-5-fluorobiphenyl-2-yl)-1-methyl-3-difluoromethyl-1H-pyrazole-4-carboxamide, N-(4'-fluoro-4-fluorobiphenyl-2-yl)-1-methyl-3-trifluoromethyl-1H-pyrazole-4-carboxamide, N-(4'-fluoro-5-fluorobiphenyl-2-yl)-1-methyl-3-trifluoromethyl-1H-pyrazole-4-carboxamide,N-(4'-chloro-5-fluorobiphenyl-2-yl)-1-methyl-3-trifluoromethyl-1H-pyrazole-4-carboxamide, N-(4'-methyl-5-fluorobiphenyl-2-yl)-1-methyl-3-trifluoromethyl-1H-pyrazole-4-carboxamide, N-(4'-fluoro-5-fluorobiphenyl-2-yl)-1,3-dimethyl-1H-pyrazole-4-carboxamide, N-(4'-chloro-5-fluorobiphenyl-2-yl)-1, 3-dimethyl-1H-pyrazole-4-carboxamide, N-(4'-methyl-5-fluorobiphenyl-2-yl)-1,3-dimethyl-1H-pyrazole-4-carboxamide, N-(4'-fluoro-6-fluorobiphenyl-2-yl)-1-methyl-3-trifluoromethyl-1H-pyrazole-4-carboxamide, N-(4'-chloro-6-fluorobiphenyl-2-yl)-1-methyl-3-trifluoromethyl-1H-pyrazole-4-carboxamide, N-[2-(1,1,2,3,3,3-hexafluoropropoxy)-phenyl]3-difluoromethyl-1-methyl-1H-pyrazole-4-carboxamide, N-[4'-(trifluoromethylthio)-biphenyl-2-yl]3-difluoromethyl-1-methyl-1H-pyrazole-4-carboxamide and N-[4'-(trifluoromethylthio)-biphenyl-2-yl] 1-methyl-3-trifluoromethyl-1-methyl-1H-pyrazole-4-carboxamide, wherein the fluthiacet-methyl and the HPPD inhibitor are present in a ratio between about 1:15 and 1:35, and wherein said ratio provides synergistic control of the weeds.

13. The method of claim 12, wherein the HPPD inhibitor is mesotrione and the fungicide is mefenoxam, ofurace, oxadixyl, oxycarboxin, 3-(3,5-dichlorophenyl)-N-isopropyl-2,4-dioxoimidazolidine-1-carboxamide, penthiopyrad or isopyrazam.

14. The method of claim 12, wherein the average height of the weeds is from about 4 inches to about 6 inches.

15. The method of claim 12, wherein the weeds comprise one or more selected from the group consisting of waterhemp, lambsquarters, velvetleaf, palmer amaranth, pigweed, morning glory, cocklebur, ragweed, broadleaf signalgrass, foxtail, crabgrass and volunteer soybean.

16. The method of claim 12, wherein the crop is selected from the group consisting of corn and sugarcane.

* * * * *